United States Patent [19]

Willms et al.

[11] Patent Number: 4,477,276
[45] Date of Patent: Oct. 16, 1984

[54] HETEROCYCLIC PHENYL ETHERS AND THEIR HERBICIDAL USE

[75] Inventors: Lothar Willms, Unkel; Reinhard Handte, Hofheim am Taunus; Hilmar Mildenberger, Kelkheim; Klaus Bauer, Rodgau; Hermann Bieringer, Eppstein; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 421,331

[22] Filed: Sep. 22, 1982

[30] Foreign Application Priority Data

Sep. 24, 1981 [DE] Fed. Rep. of Germany ....... 3137996

[51] Int. Cl.³ .................. C07D 498/04; C07D 513/04
[52] U.S. Cl. ........................................... 71/94; 71/90; 71/92; 546/114; 546/115; 546/116; 546/118
[58] Field of Search ...................... 546/114, 116, 115; 71/90, 94

[56] References Cited

U.S. PATENT DOCUMENTS 4,130,413 12/1978 Handte et al. ..................... 71/90

Primary Examiner—Jane T. Fan
Attorney, Agent, or Firm—Curtis, Morris & Safford

[57] ABSTRACT

Compounds of the formula

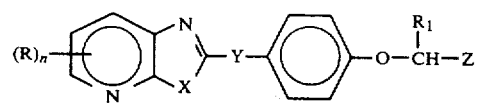

wherein R is halogen, $CF_3$, $NO_2$, CN, Alkyl or alkoxy, n is 0 to 3 X is O, S, NH or N-Alkyl, Y is O, S, SO, $SO_2$, NH or N-Alkyl, $R_1$ is H or alkyl and Z is carboxy or hydroxymethyl or functional derivatives of these groups, are valuable herbicides and growth regulators.

9 Claims, No Drawings

HETEROCYCLIC PHENYL ETHERS AND THEIR HERBICIDAL USE

The present invention relates to new 4-phenoxyalkanecarboxylic acid derivatives which contain heterocyclic substituents and have the general formula

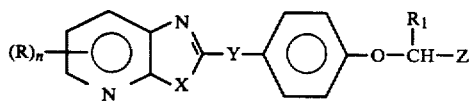

in which R denotes halogen, $CF_3$, $NO_2$, CN, $(C_1-C_4)$-alkyl or $(C_1-C_4)$-alkoxy, X denotes O, S, NH or N-$(C_1-C_4)$-alkyl, Y denotes O, S, SO, $SO_2$, NH or N-$(C_1-C_4)$-alkyl, $R_1$ denotes H or $(C_1-C_4)$-alkyl, Z denotes a group of the formula

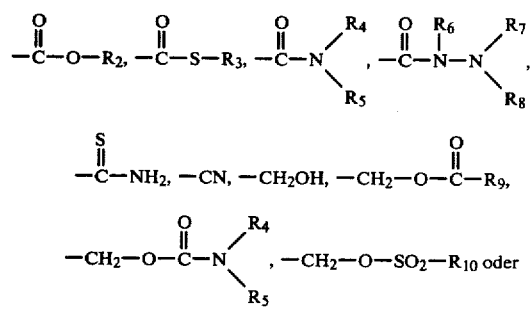

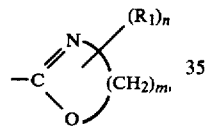

n denotes 0 to 3, m denotes 2 or 3, $R_2$ denotes H, $(C_1-C_{12})$-alkyl which is optionally substituted by 1–6 halogen atoms, preferably F, Cl, Br, and/or by OH, CN, SCN, $(C_1-C_6)$-alkoxy, $(C_1-C_4)$-alkylthio, $(C_1-C_4)$-alkylsulfinyl, $(C_1-C_4)$-alkylsulfonyl, $(C_1-C_6)$-alkoxy-$(C_2-C_6)$-alkoxy, halogeno-$(C_1-C_2)$-alkoxy methoxyethoxy, $(C_1-C_4)$-alkylamino, di-$(C_1-C_4)$-alkylamino, phenyl, oxiranyl and/or phenoxy, it being possible for the latter also to be monosubstituted or disubstituted by halogen, $(C_1-C_4)$-alkyl, —$COOR_3$ or —CO—$R_3$; or $(C_5-C_6)$-cycloalkyl which is optionally substituted by halogen or methyl; $(C_3-C_6$-alkenyl, halogeno-$(C_3-C_6)$-alkenyl or $(C_5-C_6)$-cycloalkenyl; $(C_3-C_4)$-alkinyl which is optionally monosubstituted or disubstituted by $(C_1-C_6)$-alkyl, phenyl, halogen or $(C_1-C_2)$-alkoxy; phenyl which is optionally monosubstituted to trisubstituted by $(C_1-C_4)$-alkyl, $(C_1-C_4)$-alkoxy, halogen, $NO_2$ or $CF_3$; or furfuryl, tetrahydrofurfuryl, a cation equivalent of an organic or inorganic base or one of the groups

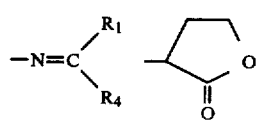

$R_3$ denotes H, $(C_1-C_6)$-alkyl or phenyl-$(C_1-C_2)$-alkyl in which the phenyl radical can be monosubstituted or disubstituted by $(C_1-C_4)$-alkyl and/or halogen; or $(C_3-C_6)$-alkenyl or phenyl which can also be monosubstituted or disubstituted by $(C_1-C_4)$-alkyl and/or halogen, $R_4$ and $R_5$ are identical or different and denote H, $(C_1-C_6)$-alkyl, hydroxy-$(C_1-C_6)$-alkyl, $(C_5-C_6)$-cycloalkyl or phenyl which is optionally monosubstituted to trisubstituted by $(C_1-C_4)$-alkyl, $(C_1-C_4)$-alkoxy, halogen or $CF_3$, subject to the proviso that $R_4$ and $R_5$ are not jointly phenyl, or $R_4$ and $R_5$ together form a methylene chain which has 2, 4 or 5 members and in which a CH group can optionally be replaced by O, NH or N($CH_3$), and, in the event that $R_4=R_1$, $R_5$ can also denote $(C_1-C_4)$-alkoxycarbonyl-$(C_1-C_4)$-alkyl, $R_6$ denotes H or $CH_3$, $R_7$ denotes H, $CH_3$ or $C_2H_5$, $R_8$ denotes H, $CH_3$, $C_2H_5$ or phenyl, $R_9$ denotes $(C_1-C_6)$-alkyl which is optionally monosubstituted to trisubstituted by halogen; or cyclopropyl, $(C_3-C_6)$-alkenyl, phenyl, $(C_1-C_4)$ alkylphenyl, $(C_1-C_4)$-alkoxyphenyl, halogenophenyl, trifluoromethylphenyl or nitrophenyl, and $R_{10}$ denotes $(C_1-C_4)$-alkyl or phenyl which can also be monosubstituted or disubstituted by halogen, $CF_3$, $NO_2$ or $(C_1-C_4)$-alkyl.

The alkyl, alkenyl and alkinyl radicals listed in the radicals $R_1-R_5$, $R_9$ and $R_{10}$ can be either straight-chain or branched. Particularly preferred compounds are those in which R=halogen and Z=COOH or COO($C_1-C_4$)-alkyl.

The invention also relates to processes for the preparation of the compounds of the formula I, which comprise, in the event that Y=O, NH or N-$(C_1-C_4)$-alkyl, (a) reacting compounds of the formula

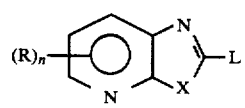

in which L is a detachable group, such as, for example, halogen, $(C_1-C_4)$-alkylsulfonyl, phenylsulfonyl, $(C_1-C_4)$-alkoxycarbonylmethylsulfonyl, $(C_1-C_4)$-alkylsulfinyl, $(C_1-C_4)$-alkylthio and the mesyl or tosyl radical, with compounds of the formula

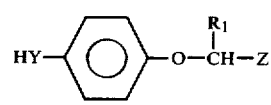

or (b) reacting compounds of the formula

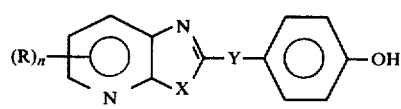

with compounds of the formula

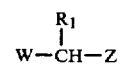

in which W represents halogen (preferably chlorine or bromine) or the mesyl or tosyl radical, or, in the event that Y=S, (c) reacting compounds of the formula

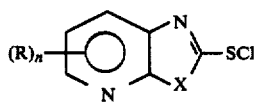

with compounds of the formula

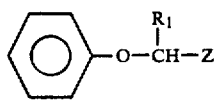

or, in the event that Y=SO and SO₂, (d) reacting compounds which have been obtained by process (c) with suitable oxidizing agents or (e) hydrogenating compounds of the formula I in which Z represents the —COOR₂ group and converting the resulting alcohols (Z=—CH₂OH), if desired, into the corresponding carboxylic acid esters (Z=—CH₂—O—C—(O)—R₉) by reaction with carboxylic acids or carboxylic acid halides or anhydrides, into sulfonic acid esters (Z=—CH₂—O—SO₂—R₁₀) by reaction with sulfonyl halides, or into carbamic acid esters

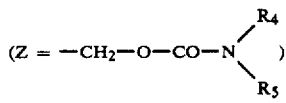

by reaction with carbamoyl halides or isocyanates, or (f) converting the compounds obtained in accordance with processes (a) to (d) into other compounds, according to the invention, of the formula I by saponification, salt formation, preparation of the acid chloride and reacting the latter with alcohols, thiols and amines, esterification, transesterification, amidation, liberation or addition of the elements of water or addition of the elements of hydrogen sulfide.

Notes on (a) and (b)

The reaction of the compounds II and III and of IV and V is preferably effected in inert, aprotic solvents, such as aliphatic or aromatic hydrocarbons (such as, for example, benzene, toluene or xylene), acid nitriles, such as, for example, acetonitrile or propionitrile, ketones, such as, for example, acetone, methyl ethyl ketone or methyl isobutyl ketone, acid amides, such as, for example, dimethylformamide, dimethylacetamide, N-methylpyrrolidone or hexamethylphosphoric acid triamide, or in dimethyl sulfoxide at temperatures between 30° and 250° C. or at the boiling point of the solvent, preferably between 60° and 160° C., and in the presence of inorganic or organic bases, such as, for example, metal alcoholates, tertiary amines, alkali metal carbonates and hydroxides or alkaline earth metal carbonates and hydroxides (NaOH or KOH).

Note on (c)

The reaction of the compounds VI and VII is carried out under the conditions of a Friedel-Crafts synthesis in the presence of Lewis acids, in inert solvents, such as aliphatic or aromatic hydrocarbons, halogenated hydrocarbons (for example CHCl₃ or CCl₄) or cyclic ethers (for example dioxane or THF) at reflux temperatures.

Note on (e)

The reduction of acids or esters to give alcohols is preferably carried out using complex metal hydrides, such as LiAlH₄, in ether-like, anhydrous solvents. Since the reaction usually takes place in an exothermic manner, an external supply of heat is generally unnecessary. The subsequent esterification with acid anhydrides or acid halides is carried out in inert solvents (as in the case of a)) at temperatures between 0° C. and the boiling point of the solvent, with the addition of an organic or inorganic base, for example Na₂CO₃, K₂CO₃, pyridine or triethylamine. The esterification with carboxylic acids is carried out either by adding water-binding agents, such as P₂O₅, or by azeotropic extractive distillation of the acidified components. Carbamoyl halides and isocyanates can be reacted with the alcohols in the presence of bases under conditions similar to those of carboxylic acid halides, somewhat elevated temperatures generally being used, preferably temperatures between 40° C. and the boiling point of the solvent.

Note on (f)

For the amidation of compounds of the formula I it is possible, firstly, to use esters as the starting material and to react these with amines, ammonia or hydrazines. In this case it is preferable to use the same solvents as in the case of (a) and to carry out the reaction at temperatures between 40° C. and reflux temperature. It is also possible, however, first to convert acids of the formula I into acid halides in a known manner and then to react the latter with ammonia, amines or hydrazines. At least a molar excess of the base employed is necessary in order to bind the hydrogen halide liberated. Other esters or thioesters of the formula I can be obtained by reacting the acid chloride with alcohols or mercaptans.

The transesterification is effected by acid or base catalysis. It is advantageous to add an excess of the alcohol which is to be introduced into the ester and to distil off continuously the lower-boiling alcohol liberated, at the rate at which it is formed in the transesterification.

The dehydration of amides to give nitriles is preferably carried out in aromatic hydrocarbons at temperatures of 50° C. up to the boiling point. The subsequent addition reaction with H₂S is advantageously carried out in an autoclave in the presence of catalytic quantities of a base (preferably ethanolamine), at temperatures between 50° and 150° C.

The heterocyclic compounds of the formula II which are required for the preparation of the compounds, according to the invention, of the general formula I represent, in accordance with the definition of X, suitably substituted 2-halogeno-oxazolo[5,4-b]pyridines, -thiazol[5,4-b]pyridines or imidazolo[5,4-b]pyridines, 2alkylsulfonyl-oxazolo[5,4-b]pyridines, -thiazolo[5,4-b]pyridines or -imidazolo[5,4-b]pyridines, 2-phenylsulfonyloxazolo[5,4-b]pyridines, -thiazolo[5,4-b]pyridines or -imidazolo[5,4-b]pyridines, 2-alkoxycarbonylmethylsulfonyloxazolo[5,4-b]pyridines, -thiazolo-[5,4-b]pyridines or -imidazolo[5,4-b]pyridines, 2-alkylsulfinyloxazolo[5,4-b]pyridines, -thiazol[5,4-b]pyridines or -imidazolo[5,4-b]pyridines, 2-alkylthio-oxazolo[5,4-b]pyridines, -thiazolo[5,4-b]pyridines or -imidazolo[5,4-b]pyridines, 2-mesyloxazolo[5,4-b]pyridines, -thiazolo[5,4-b]pyridines or -imidazolo[5,4-b]pyridines or 2-tosyl-oxazolo[5,4-b]pyridines, -thiazolo[5,4-b]pyridines or -imidazolo[5,4-b]pyridines, which are prepared by known processes, for example from the corresponding 2-mercapto compounds or 2-hydroxy compounds by halogenation or from the corresponding 2-mercapto compounds by alkylation and oxidation (cf., for example, Chem. Pharm. Bull 7, 720 (1959); Chem. Pharm. Bull 3, 356 (1955); or J. Pharm. Soc. Japan 71, 920 (1951)).

The corresponding phenols of the formulae III and IV (X=O) can be prepared, for example, by monoalkylation of hydroquinone (J. Org. Chem. 39, page 214 (1974) or Soc. 1965, 954–73). The sulfenyl chlorides of the formula VI can be prepared, for example, from the disulfides or mercaptans by reaction with chlorine (Houben-Weyl IX, page 269). The ethers of the formula VII are advantageously prepared by reacting phenol with compounds of the general formula

in which B denotes halogen or a sulfo ester group.

If $R_1$ is not hydrogen, the compounds of the formula I have a center of asymmetry and are usually in a racemic form. The racemates can be separated into diastereomers by customary methods. Equally, however, it is also possible to employ optically active starting materials in the processes mentioned; this is particularly suitable for the reactions according to (a) or (b), the compounds III and V being employed in an optically active form. The invention relates to both the racemates and the optical antipodes, especially the D-forms of the latter.

The compounds, according to the invention, of the general formula I have a very good action in the pre-emergence and post-emergence techniques against a broad spectrum of annual and perennial graminaceous weeds, but are at the same time excellently tolerated by dicotyledonous crop plants and by some species of cereals. The compounds are therefore suitable for selectively combating annual and perennial graminaceous weeds in crop plants. Examples of such graminaceous weeds are wild oats (Avena), foxtail (Alopecurus spp.), meadow grass (Poa spp.), rye grass (Lolium spp.), annual and perennial wild millets (Echinochloa spp.), Setaria spp., Digitaria spp., Panicum spp., Sorghum spp., Bermuda grass (Cynodon spp.) and wheatgrass (Agropyron spp.).

Typical growth-regulating effects can be observed when the compounds according to the invention are used in sub-toxic doses; thus it is possible, for example, to affect the growth of plants and also the constituents of plants. The compounds are therefore suitable for use as growth regulators in crops of useful plants, such as, for example, cereals, maize, sugar cane, tobacco, rice and sorghum. On the other hand, it is also possible to control plant crops, such as cultivated lawns or plant communities on the edges of paths and roads and also ornamental plants.

The present invention also relates, therefore, to herbicidal and growth-regulating agents which contain a herbicidal quantity, or a quantity which has a growth-regulating action, of a compound of the general formula I, together with customary additives and formulation auxiliaries.

The agents according to the invention generally contain 2–95% by weight of the active compounds of the formula I. They can be used in the customary preparations in the form of wettable powders, emulsifiable concentrates, atomizable solutions, dusting agents or granules.

Wettable powders are preparations which can be dispersed uniformly in water and which, besides the active compound and as well as a diluent or inert substance, also contain wetting agents, for example polyoxyethylated alkylphenols, polyoxyethylated oleylamines, stearylamines, alkylsulfonates or alkylphenylsulfonates and dispersing agents, for example sodium lignin sulfonate, sodium 2,2'-dinaphthylmethane-6,6'-disulfonate or sodium oleoylmethyltauride.

Emulsifiable concentrates are obtained by dissolving the active compound in an organic solvent, for example butanol, cyclohexanone, dimethylformamide, xylene or higher-boiling aromatic compounds, and adding a non-ionic wetting agent, for example a polyoxyethylated alkylphenol or a polyoxyethylated oleylamine or stearylamine.

Dusting agents are obtained by grinding the active compound with finely divided solid substances, for example talc, natural clays, such as kaolin, bentonite or pyrophillite, or diatomaceous earth.

Atomizable solutions, such as are frequently sold in spray cans, contain the active compound dissolved in an organic solvent, together with, for example as a propellent, a mixture of fluorochlorohydrocarbons.

Granules can be prepared either by atomizing the active compound onto an adsorbent, granulated inert material or by applying active compound concentrates to the surface of carriers, such as sand or kaolinite, or a granulated inert material, by means of adhesives, for example polyvinyl alcohol, sodium polyacrylate or mineral oils. It is also possible to prepare suitable active compounds in the manner customary for the production of fertilizer granules—if desired as a mixture with fertilizers.

In the case of the herbicidal agents, the concentrations of the active compounds can vary in commercial formulations. In wettable powders, the concentration of active compound varies, for example, between about 10% and 95%, the remainder is composed of the formulation additives indicated above. In the case of emulsifiable concentrates, the concentration of active compound is about 10% to 80%. Formulations in the form of dusts contain in most cases 5–20% of active compound, while atomizable solutions contain about 2–20%. In the case of granules, the content of active compound depends to some extent on whether the active compound is in a liquid or solid form and on the granulating auxiliaries, fillers etc. which are used.

For application, the commercially available concentrates are, if appropriate, diluted in a customary manner, for example with water in the case of wettable powders and emulsifiable concentrates. Preparations in the form of dusts and granules and also atomizable solutions are not diluted further with additional inert substances before use. The application rate required varies with the external conditions such as temperature, humidity and other conditions. It can vary within wide limits and is 0.01 to 10 kg/hectare for herbicidal agents and 0.001–1 kg/hectare for growth-regulating agents.

The active compounds according to the invention can be combined with other herbicides, insecticides and fungicides.

FORMULATION EXAMPLES

Example A

An emulsifiable concentrate is obtained from 15 parts by weight of active compound, 75 parts by weight of cyclohexanone, as solvent, and 10 parts by weight of oxethylated nonylphenol (10 EO), as emulsifier.

Example B

A wettable powder which can be dispersed easily in water obtained by mixing 25 parts by weight of active compound, 64 parts by weight of kaolin-containing quartz, as inert material, 10 parts by weight of calcium lignin sulfonate and 1 part by weight of sodium oleoyl-methyltauride, as wetting agent and dispersing agent, and grinding the mixture in a pin disk mill.

Example C

A dusting agent is obtained by mixing 10 parts by weight of active compound and 90 parts by weight of talc, as inert material, and comminuting the mixture in a beater mill.

Example D

Granules are composed, for example, of about 2–15 parts by weight of active compound and 98–85 parts by weight of inert granular materials, such as, for example, attapulgite, pumice stone and quartz sand.

PREPARATION EXAMPLES

Example 1

Ethyl 2-[4-(5-chlorothiazolo[5,4-b]pyridin-2-yloxy)phenoxy]-propionate 21 g (0.1 mole) of ethyl 2-(4'-hydroxyphenoxy)propionate were heated under reflux for 1 hour with 16.6 g (0.12 mole) of potassium carbonate in 250 ml of acetonitrile in order to form the salt. After adding 24.9 g (0.1 mole) of 2-methylsulfonyl-5-chlorothiazolo[5,4-b]pyridine, the reaction mixture was heated under reflux for a further 10 hours. The salt constituent was filtered off while hot and the solvent was removed. The residue was distilled in a high vacuum. This gave 33.6 g (89% of theory) of ethyl 2-[4-(5-chlorothiazolo[5,4-b]pyridin-2-yloxy)-phenoxy]-propionate, of boiling point 204°–207° C./0.01 mbar, which crystallized completely after a little time (melting point 60°–62° C.).

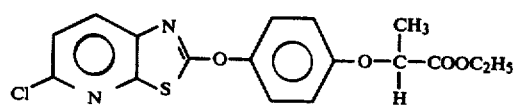

Example 2

Butyl 2-[4-(5-chlorothiazolo[5,4-b]pyridin-2-yloxy)phenoxy]-propionate (a) 2-[4-(5-Chlorothiazolo[5,4-b]pyridin-2-yloxy)phenoxy]-propionic acid 37.8 g (0.1 mole) of ethyl 2-[4-(5- chlorothiazolo[5,4-b]pyridin-2-yloxy)-phenoxy]-propionate from Example 1 were stirred with 4.4 g (0.11 mole) of sodium hyroxide in 250 ml of water for 24 hours at approximately 30° C. The slightly cloudy solution was filtered, 500 ml of toluene were then added and the mixture was warmed to 80° C. and its pH was adjusted to 1 with concentrated hydrochloric acid. The phases were separated while hot, the water phase was again stirred thoroughly with 250 ml of toluene under hot conditions, and the combined toluene phases were dried azeotropically and concentrated to a volume of approximately 250 ml.

(b) Preparation of the acid chloride of (a)

14.3 g (0.12 mole) of thionyl chloride were added at approximately 70° C. to the acid obtained in accordance with (a), in toluene. After the addition, the mixture was heated under reflux until the evolution of gas was complete (duration approximately 7 hours). Excess thionyl chloride and a little toluene were distilled off and the resulting solution of the acid chloride was reacted without further treatment.

(c) Conversion of the acid chloride from (b)

200 ml of the solution of acid chloride from (b) (0.1 mole) were initially taken at approximately 25° C. and 11 g (0.11 mole) of triethylamine and 7.4 g (0.1 mole) of butanol, dissolved in 100 ml of toluene, were added. After the addition, the mixture was stirred for 2 hours at 60° C., and was cooled and the hydrochloride formed was removed by adding 200 ml of water. After separation, the organic phase was dried and concentrated, and the residue which remained was distilled. Distillation gave 34.6 g (85% of theory) of butyl 2-[4-(5-chlorothiazolo[5,4-b]pyridin-2-yloxy)-phenoxy]-propionate of boiling point 225°–230° /0.1 mbar.

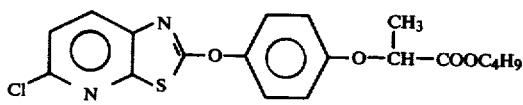

The following compounds of the general formula

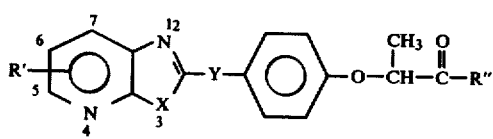

were obtained analogously in accordance with preparation examples 1 and 2.

TABLE 1

Compounds of the general formula

| Example serial number | R' | X | Y | R'' | Bp; Mp; $n_D$ [°C.] |
|---|---|---|---|---|---|
| 3 | H | S | O | —OC$_2$H$_5$ | Bp 196-198° C./0.1 mbar |
| 4 | 5-Cl | S | O | —OCH$_3$ | |
| 5 | 5-F | S | O | —O—CH$_2$—CH=CH$_2$ | |
| 6 | 5-Cl | S | O | —O—CH$_2$—CH$_2$—OCH$_3$ | |
| 7 | 5-Cl | S | O | —NH$_2$ | |
| 8 | 5-F | S | O | —NH—CH$_3$ | |
| 9 | 5-Cl | S | O | —OH | |
| 10 | 5-Cl | S | O | —ONa | |
| 11 | 5-Cl | S | O | —O—N=C(CH$_3$)$_2$ | |
| 12 | 5-Cl | S | O | —S—C$_2$H$_5$ | |
| 13 | 5-Cl | O | O | —OCH$_3$ | |
| 14 | 5-Cl | O | O | —OC$_2$H$_5$ | |
| 15 | 6-Cl | O | O | —O—CH$_2$—C≡CH | |
| 16 | H | O | O | —O—C$_4$H$_9$ | |
| 17 | 5-Cl | O | O | —OH | |
| 18 | 5-Cl | O | O | —OK | |
| 19 | 5-Cl | O | O | —O—⟨C$_6$H$_5$⟩ | |
| 20 | 5-F | O | O | —O—CH$_2$—CH$_2$—CH$_2$Cl | |
| 21 | 5-Cl | S | NCH$_3$ | —OCH$_3$ | |
| 22 | 5-Cl | S | NCH$_3$ | —OC$_2$H$_5$ | |
| 23 | 5-Cl | O | NCH$_3$ | —OC$_4$H$_9$ | |
| 24 | 5-Cl | O | O | O—N=C(CH$_3$)$_2$ | |

BIOLOGICAL EXAMPLES

Example I

Pre-emergence treatment

Seeds of grasses were sown in pots and the preparations according to the invention, formulated as wettable powders or as emulsion concentrates, were sprayed onto the surface of the cultivated soil at various dosages. The pots were then placed in a greenhouse for 4 weeks and the result of the treatment was recorded (as were also the examples which follow) by means of a rating in accordance with the system below:

1—0-20% damage
2—20-40% damage
3—40-60% damage
4—60-80% damage
5—80-100% damage

The preparations according to the invention exhibited a good action against annual graminaceous weeds and, in some cases, also against perennial graminaceous weeds; the test plants used were Avena, Alopecurus, Lolium, Echinochloa, Setaria, Agropyron and Cynodon. Application rates of 2.4 kg/hectare of active ingredient led nearly always to damage within the range of ratings 4 and 5.

TABLE I

Pre-emergence treatment (dosage: 2.4 kg/hectare of active substance)

| Compound (Example) | AVF | ALM | SAL | LOM | ECG | AGR | CND* |
|---|---|---|---|---|---|---|---|
| 1 | 5 | 5 | 5 | 5 | 5 | 5 | 4 |

TABLE I-continued

Pre-emergence treatment (dosage: 2.4 kg/hectare of active substance)

| Compound (Example) | AVF | ALM | SAL | LOM | ECG | AGR | CND* |
|---|---|---|---|---|---|---|---|
| 2 | 5 | 5 | 5 | 5 | 5 | 5 | 4 |

*AVF Avena
ALM Alopecurus
SAL Setaria
LOM Lolium
ECG Echinochloa
AGR *Agropyron repens*
CND *Cynodon dactylon*

Example II

Post-emergence treatment

Seeds of grasses were sown in pots and cultivated in a greenhouse. 3 weeks after sowing, the preparations according to the invention, formulated as wettable powders or as emulsion concentrates, were sprayed onto the plants at various dosages, and the action of the preparations was given a rating after a waiting period in the greenhouse of 4 weeks.

The agents according to the invention had a good herbicidal action against a broad spectrum of annual graminaceous weeds. Furthermore, some preparations also combated the perennial graminaceous weeds Cynodon dactylon, Sorghum halepense and Agropyron repens.

TABLE II

| Post-emergence action (dosage: 2.4 kg/hectare of active substance) | | | | |
|---|---|---|---|---|
| Compound (Example) | ALM | SAL | LOM | ECG |
| 1 | 5 | 5 | 5 | 5 |
| 2 | 5 | 5 | 5 | 5 |

Example III

Toleration by crop plants

In further tests in a greenhouse, seeds of a fairly large number of crop plants were laid out in pots. Some of the pots were treated immediately, the remainder were placed in a greenhouse until the plants had developed 2 to 3 true leaves, and were then sprayed with substances according to the invention.

The results, which were recorded 4 to 5 weeks after application, show that the substances according to the invention leave dicotyledonous crops completely or almost completely unharmed even at 2.4 kg/hectare in the pre-emergence and post-emergence techniques. In addition, some substances also spare graminaceous crops such as barley, sorghum, maize, wheat or rice.

The substances are thus highly selective in respect of the weed-killing action described in the preceding examples.

We claim:

1. A 4-phenoxyalkanecarboxylic acid compound of the formula

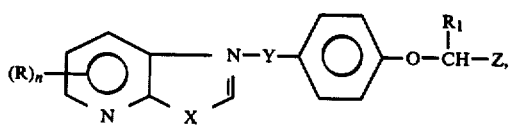

wherein

R is halogen, $CF_3$, $NO_2$, CN, $(C_1-C_4)$-alkayl, or $(C_1-C_4)$-alkoxy, and n is 0 to 3;
X is S or O;
Y is O, S, SO, $SO_2$, NH, or N-$(C_1-C_4)$-alkyl;
$R_1$ is H or $(C_1-C_4)$-alkyl; and

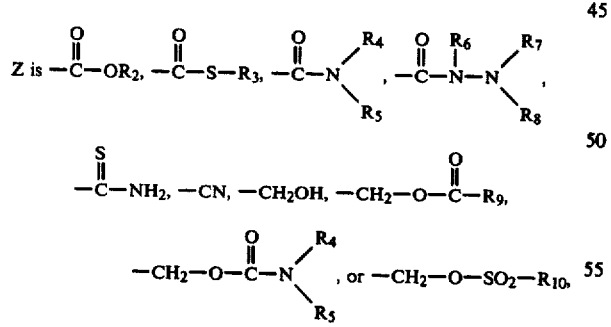

wherein
$R_2$ is
 H,
 $(C_1-C_{12})$-alkyl,
 $(C_1-C_{12})$-alkyl substituted by at least one member selected from the group consisting of up to 6 halogen atoms,
 OH,
 CN,
 SCN,
 $(C_1-C_6)$-alkoxy,
 $(C_1-C_4)$-alkylthio,
 $(C_1-C_4)$-alkylsulfinyl,
 $(C_1-C_4)$-alkylsulfonyl,
 $(C_1-C_6)$-alkoxy-$(C_2-C_6)$-alkoxy,
 halogeno-$(C_1-C_2)$-alkoxy,
 methoxyethoxyethoxy,
 $(C_1-C_4)$-alkylamino,
 di-$(C_1-C_4)$-alkylamino,
 phenyl,
 phenoxy,
 phenyl or phenoxy mono- or disubstituted by
  halogen,
  $(C_1-C_4)$-alkyl,
  $COOR_3$, or
  $-CO-R_3$,
 $(C_5-C_6)$-cycloalkyl,
 $(C_5-C_6)$-cycloalkyl substituted by
  halogen or
  methyl,
 $(C_3-C_6)$-alkenyl,
 halogeno-$(C_3-C_6)$-alkenyl,
 $(C_5-C_6)$-cycloalkenyl,
 $(C_3-C_4)$-alkinyl,
 $(C_3-C_4)$-alkinyl mono- or di-substituted by
  $(C_1-C_6)$-alkyl,
  phenyl,
  halogen,
  $(C_1-C_2)$-alkoxy,
 phenyl,
 phenyl mono-, di-, or tri-substituted by
  $(C_1-C_4)$-alkyl,
  $(C_1-C_4)$-alkoxy,
  halogen,
  $NO_2$ or
  $CF_3$,
 a cation equivalent of organic or inorganic base, or
 $-N=C(R_1)(R_4)$;
$R_3$ is
 H,
 $(C_1-C_4)$-alkyl,
 phenyl-$(C_1-C_2)$-alkyl,
 phenyl-$(C_1-C_2)$-alkyl mono- or di-substituted by at least one member selected from the group consisting of
  $(C_1-C_4)$-alkyl and
  halogen,
 $(C_3-C_6)$-alkenyl,
 phenyl,
 phenyl mono- or di-substituted by at least one member selected from the group consisting of
  $(C_1-C_4)$-alkyl and
  halogen;
$R_4$ and $R_5$, taken alone, are the same or different and are
 H,
 $(C_1-C_6)$-alkyl,
 hydroxy-$(C_1-C_6)$-alkyl,
 $(C_5-C_6)$-cycloalkyl,
 phenyl, or
 phenyl mono- di-, or tri-substituted by
  $(C_1-C_4)$-alkyl,
  $(C_1-C_4)$-alkoxy,
  halogen, or
  $CF_3$,
but $R_4$ and $R_5$ are not both phenyl or substituted phenyl, and if $R_4$ is H or $(C_1-C_4)$-alkyl, the $R_5$ may be $(C_1-C_4)$-alkoxycarbonyl-$(C_1-C_4)$-alkyl;

$R_6$ is H or $CH_3$;

$R_7$ is H, $CH_3$ or $C_2H_5$;

$R_8$ is H, $CH_3$, $C_2H_5$, or phenyl;

$R_9$ is (C$_1$-C$_4$)-alkyl, (C$_1$-C$_4$)-alkyl mono-, di- or trisubstituted by halogen, cyclopropyl, (C$_3$-C$_6$)-alkenyl, phenyl, or phenyl mono-substituted by (C$_1$-C$_4$)-alkyl, (C$_1$-C$_4$)-alkoxy, halogen, CF$_3$, or nitro; and $R_{10}$ is (C$_1$-C$_4$)-alkyl, phenyl, or phenyl mono- or di-substituted by halogen,

CF$_3$,

NO$_2$, or (C$_1$-C$_4$)-alkyl.

2. A compound as in claim 1 wherein R is hydrogen (n=0) or chlorine in the 5-position (n=1), Y is oxygen, $R_1$ is CH$_3$, and Z is —COOH or —COO—(C$_1$-C$_4$)-alkyl.

3. A compound as in claim 1 which is

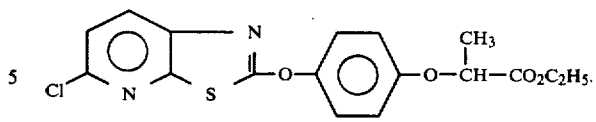

4. A compound as in claim 1 which is

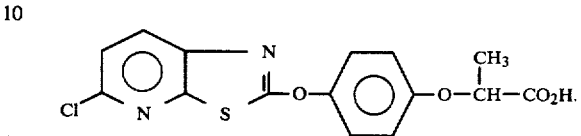

5. A compound as in claim 1 which is

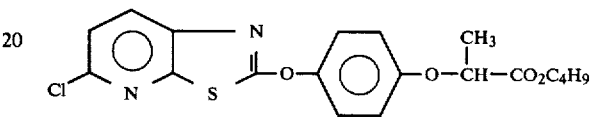

6. A herbicidal composition which comprises a herbicidally effective amount of a compound as in claim 1 and a carrier therefor.

7. A growth regulating composition which comprises a compound as in claim 1 in an amount which is effective to regulate growth and a carrier therefor.

8. A method for combatting undesirable plant growth which comprises applying a herbicidally effective amount of a compound as in claim 1 to the undesirable plants or to the area on which they grow.

9. A method for regulating the growth of useful plants which comprises applying to said plants a compound as in claim 1 in an amount effective to regulate growth.

* * * * *

UNITED STATES PATENT AND TRADEMARK OFFICE
CERTIFICATE OF CORRECTION

PATENT NO. : 4,477,276
DATED : October 16, 1984
INVENTOR(S) : Lothar Willms et al.

It is certified that error appears in the above-identified patent and that said Letters Patent are hereby corrected as shown below:

Claim 1, line 3, change

" 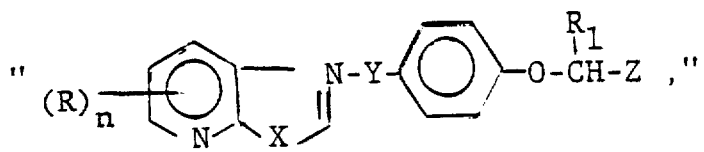 ,"

to -- 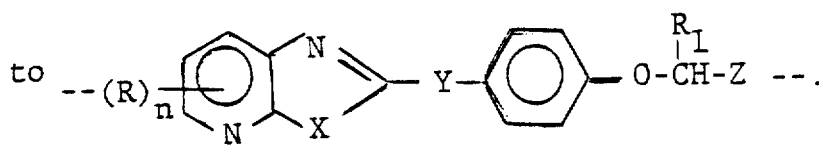 --.

Signed and Sealed this

First Day of November, 1988

Attest:

DONALD J. QUIGG

Attesting Officer    Commissioner of Patents and Trademarks